United States Patent [19]

Millar

[11] Patent Number: 4,901,731
[45] Date of Patent: Feb. 20, 1990

[54] SINGLE SENSOR PRESSURE DIFFERENTIAL DEVICE

[75] Inventor: Huntly D. Millar, Houston, Tex.

[73] Assignee: Millar Instruments, Inc., Houston, Tex.

[21] Appl. No.: 186,898

[22] Filed: Apr. 27, 1988

[51] Int. Cl.$^4$ .................................................. A61B 5/02
[52] U.S. Cl. .................................... 128/675; 128/673; 128/748
[58] Field of Search ................................ 128/672–675, 128/748, 772, 656–658, 344; 604/95–103

[56] References Cited

U.S. PATENT DOCUMENTS

| | | |
|---|---|---|
| 3,088,323 | 5/1963 | Welkowitz et al. |
| 3,350,944 | 11/1967 | DeMichele |
| 3,490,441 | 1/1970 | Curtis |
| 3,553,625 | 1/1971 | Stedman |
| 3,710,781 | 1/1973 | Huthcins et al. |
| 3,724,274 | 4/1973 | Millar |
| 3,748,623 | 7/1973 | Millar |
| 3,811,427 | 5/1974 | Kresse |
| 3,971,364 | 7/1976 | Fletcher et al. |
| 4,274,423 | 6/1981 | Mizuno et al. |
| 4,456,013 | 6/1984 | De Rossi et al. |
| 4,545,390 | 10/1985 | Leary ............................. 128/657 X |
| 4,601,706 | 7/1986 | Aillon ............................ 128/673 X |
| 4,621,646 | 11/1986 | Bryant ........................... 128/673 X |
| 4,641,654 | 2/1987 | Samson et al. ................. 128/657 X |
| 4,718,423 | 1/1988 | Willis et al. ................... 128/673 X |
| 4,718,425 | 1/1988 | Tanaka et al. ................. 128/673 |

FOREIGN PATENT DOCUMENTS 2420610 10/1975 Fed. Rep. of Germany .
2708607 9/1977 Fed. Rep. of Germany .

OTHER PUBLICATIONS

Matsumoto et al., "Development of a Fibre Optic Catheter Tip Press Transducer", J. Med. Eng. and Technol., vol. 2, No. 5, 9–1978, pp. 239–242.
Philips Microtransducer Catheter Brochure.
New Microtransducer Catheter, Philips Medical Systems, 1982.
Gaeltec Catheter Transducers Manual.
Gaeltec Ltd.

Primary Examiner—Angela D. Sykes
Attorney, Agent, or Firm—Arnold, White & Durkee

[57] ABSTRACT

An apparatus and method for sensing in vivo the fluid pressure differential between spaced locations in a biological fluid vessel using a single pressure transducer. The transducer has a deformable member mounted to a housing; a conduit extends within the housing with one end opening at a location spaced from the transducer and the other end opening adjoining the inner surface of the member. With the housing inserted in the biological fluid vessel, the outer surface of the deformable member is exposed to the fluid pressure adjacent the member, while the inner surface is exposed to the fluid pressure within the conduit. The deformable member flexes in response to the fluid pressure differential across the member, which is a direct measure of the fluid pressure differential between spaced-apart locations in the fluid-filled vessel. Strain gauges are mounted to the member to generate a signal indicative of the pressure differential, with electrical leads coupled to the strain gauges and received in a catheter threaded in the vessel. In a preferred embodiment, the transducer is mounted proximal to an angioplasty balloon and the conduit opens distal to the balloon. This arrangement can give a pressure differential across a lesion with the balloon positioned adjacent the lesion in the coronary arterial tree. This pressure differential apparatus is not only reliable, durable, and accurate, but also permits reduced catheter size and profile facilitating insertion and manipulation in blood vessels.

29 Claims, 2 Drawing Sheets

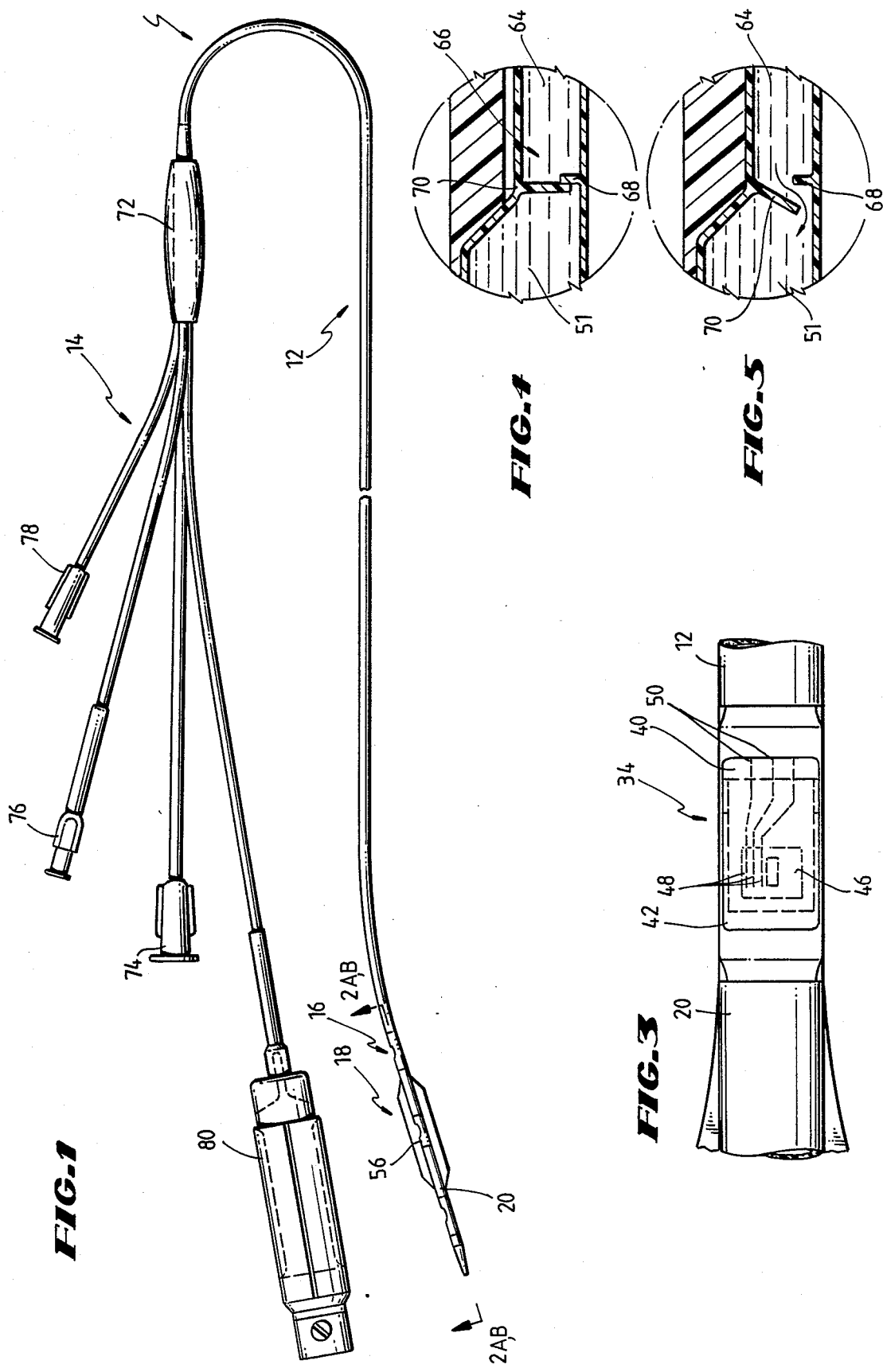

SINGLE SENSOR PRESSURE DIFFERENTIAL DEVICE

BACKGROUND OF THE INVENTION

1. Field of the Invention

The present invention relates to a method and apparatus for determining the pressure differential between two spaced locations in a fluid-filled biological vessel.

2. Description of Related Art

In recent years there has been an increased desire to obtain in vivo measurements of biological fluid pressure. Fluid pressure measurements are becoming increasingly widespread in cardiology, cardiovascular surgery, urology, gynecology, and gastroenterology. Along with the increase in demand for pressure measurements in a variety of medical applications, there has been an increased desire for greater accuracy and fidelity of such fluid pressure measurements. Further, there is an increasing desire to obtain pressure measurements in small, difficult to reach locations increasing the demand for devices of decreased size and increased maneuverability.

The most common type of device for sensing pressure is the "through the lumen" or "fluid-filled" type of catheter in which the open, distal end of the catheter tube is placed at the location where the fluid pressure is to be determined. Such fluid-filled types of pressure sensing catheters extend from the location where the fluid pressure is to be determined, to an external pressure transducer or manometer outside the patient for recording pressure changes in the fluid-filled lumen. While such fluid-filled pressure catheters do provide a rough approximation of pressure, it is generally recognized that such fluid-filled catheters have a number of associated problems.

One problem with taking pressure measurements through the fluid-filled lumen of such a catheter is that the measurements prevent use of the lumen for other functions. For example, it might be desirable to use the lumen to receive a guidewire for steering and manipulating the catheter, or it might be desirable to use the lumen to introduce contrast medium or drugs. It is usually difficult to use the lumen for more than one function at a time, and providing multiple lumens undesirably increases the overall size of the catheter. Another problem with such catheters is that pressure tracings obtained from fluid-filled catheters are dampened because of the length of the lumen and relatively small diameter of the lumen. Such dampened pressure tracings are only useful in approximating mean pressure. In many applications it is desirable to obtain high fidelity pressure tracing to analyze the rate of pressure change (dP/dT), which is generally not possible with a fluid-filled pressure tracing. An effective barrier to further size reduction of fluid-filled catheters is presented if a fluid-filled pressure lumen having a minimum diameter (e.g., 0.5 mm) is necessary for obtaining useful pressure tracings.

One solution to the shortcomings of fluid-filled pressure catheters is the use of a pressure sensor probe. Such probes use a pressure transducer mounted on the probe which accurately measures fluid pressure in the vicinity of the transducer. For example, the MIKRO-TIP® probes made by Millar Instruments, Inc. of Houston, Texas (e.g. Model Nos. SPC-450, SPC-330) are effective in providing high fidelity pressure measurements, and may also include a separate lumen for fluid sampling or drug or contrast media injection. Other examples include U.S. Pat. Nos. 3,724,274; 4,274,423; and 4,456,013 (incorporated by reference).

In many medical applications, it is desirable not to obtain absolute pressure readings, but rather to obtain an indication of pressure gradient or differential between two locations in the vessel. For example, in coronary angioplasty, the procedure is usually monitored angiographically, with an intracoronary electrocardiogram, and with fluid pressure measurements taken distal and proximal to the stenosis. Such blood pressure measurements distal and proximal to the lesion are very important in that the transstenotic pressure gradient is an objective and accurate indication of the significance of the stenosis (*See e.g.,* B. Meier, *Coronary Angioplasty* (1987)).

Conventional methods of obtaining an indication of such pressure gradient are inefficient in several respects. If a fluid-filled lumen type of catheter is used, two separate lumens must be provided—one lumen opening at the first location of interest (e.g. proximal to the lesion) and a second lumen opening at the second location of interest (e.g. distal to the lesion). Providing two separate fluid-filled lumens undesirably increases the size of the catheter, and of course only gives a mean approximation of pressure gradient.

Using a pressure sensor type of catheter is preferable to the fluid-filled lumen approach, but still has several limitations. Such a pressure sensor catheter would include two pressure transducers spaced along the catheter to obtain an indication of absolute fluid pressure at each transducer location. Such a dual pressure sensor catheter requires that both transducers perform accurately and reliably, and the associated leads and transducer mountings give a somewhat complicated catheter assembly. Additionally, the catheter size and profile is driven by the need to accommodate both pressure transducers. Thus, transducer technology limits the size and configuration of such a two pressure sensor catheter. Catheter size and profile is a very important consideration, particularly in coronary angioplasty where the distal end of the catheter must be advanced across a lesion partially occluding the coronary vessel. Therefore, it would be desirable to develop a pressure sensor catheter which could obtain high fidelity pressure differential tracings, while minimizing the catheter size and profile constraints imposed by transducer technology.

SUMMARY OF THE INVENTION

The pressure transducer catheter of the present invention provides high fidelity tracings of pressure differential between spaced locations in a vessel, while minimizing size and profile. The catheter hereof uses only a single pressure transducer for directly sensing the fluid pressure differential between spaced locations in the vessel. By using a single pressure transducer to obtain pressure differential, the catheter size and profile is reduced, durability and reliability are increased, while fidelity is maintained.

Broadly speaking, the fluid pressure differential sensing apparatus of the present invention includes an elongated housing coupled to the distal end of an elongated catheter body. A pressure sensing transducer is coupled to the housing at a first location and includes a member which deforms in response to a fluid pressure differential thereacross. An elongated conduit is coupled to the housing and has one end opening at a second location spaced from the transducer, with the other end of the conduit opening adjacent the transducer member. Thus, the outer surface of the transducer member responds to fluid pressure adjacent the transducer, while the inner surface of the transducer member responds to the fluid pressure through the conduit. Therefore, the transducer is sensing directly the fluid pressure differential.

In a preferred form, the pressure differential sensing apparatus is incorporated into an angioplasty type catheter having a dilation balloon mounted to the housing. Preferably, the pressure transducer is mounted to the housing proximal to the dilation balloon while the conduit extends from the transducer and opens distal to the dilation balloon. When inserted in a blood vessel, the transducer yields high fidelity tracings of pressure differential between the fluid pressure distal and proximal to the dilation balloon. This is, of course, desirable during the angioplasty procedure with the dilation balloon positioned adjacent a lesion, providing transstenotic high fidelity pressure gradient tracings continuously before, during, and after dilation. The elimination of a transducer distal to the dilation balloon permits a low profile distal tip and a catheter of smaller size, facilitating transstenotic crossing and greater subselectivity.

The method of sensing pressure differential between two spaced apart locations in a biological fluid-filled vessel in accordance with the present invention incorporates a pressure sensor having a transducer, a catheter body coupled to the transducer, and an elongated conduit having one end adjoining the transducer. The method broadly includes the steps of inserting the sensor into the biological vessel with a portion of the catheter body extending from the vessel (i.e. patient). The sensor is manipulated into the region of interest in the vessel, including the substeps of positioning the transducer at a first location in the vessel and positioning the conduit open end at a second location in the vessel spaced from the first location. The conduit is filled with fluid so that the fluid within the conduit is indicative of fluid pressure at the second location. With the transducer positioned in the region of the interest and the conduit filled with fluid, the transducer is operated to sense the pressure differential between the fluid adjoining the transducer (first location) and the fluid within the conduit (second location). Preferably, the sensor is inserted using a steerable guidewire with the sensor coupled to the guidewire and advanced along the guidewire in the vessel. The conduit can be filled with fluid either by injecting a fluid down a dedicated lumen in the catheter body (in communication with the conduit) or by drawing biological fluid into the conduit from the open end.

BRIEF DESCRIPTION OF THE DRAWINGS

FIG. 1 is a fragmentary plan view of an angioplasty catheter in accordance with the present invention;

FIG. 3 is a fragmentary, top plan view of the deformable member mounted to the housing taken along line 3—3 of FIG. 2B;

FIG. 4 is an enlarged, fragmentary, vertical sectional view of the valve from FIG. 2B in a closed configuration;

FIG. 5 is an enlarged, fragmentary, vertical sectional view of the valve of FIG. 4 illustrated in its open configuration.

DESCRIPTION OF THE PREFERRED EMBODIMENTS

Figure 6:
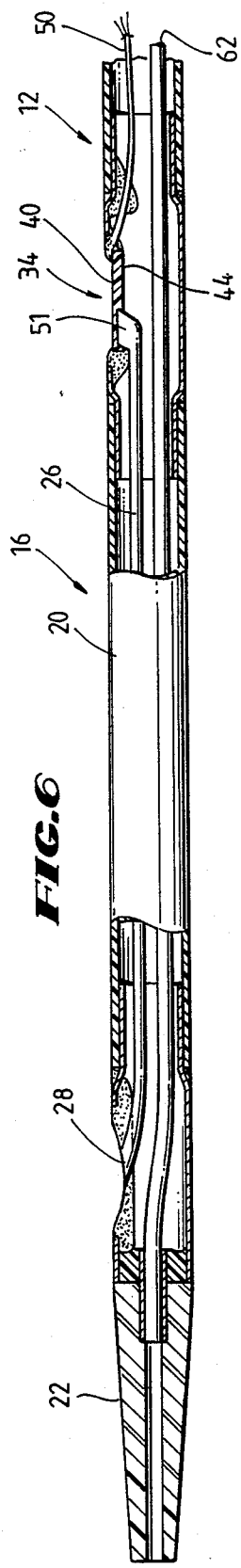
FIG. 6 is a fragmentary, elevational view in partial section illustrating the distal region of another embodiment of the pressure sensing apparatus of the present invention.

Turning now to the drawings, an apparatus 10 for sensing the fluid pressure differential between spaced locations is illustrated. The apparatus 10 illustrated is a coronary angioplasty type of catheter and includes an elongated catheter body 12 receivable in a fluid-filled biological vessel, an interface section 14 coupled to the proximal end of the catheter body 12, and sensor mechanism 16 and dilation mechanism 18 coupled to the distal end of the catheter body 12. FIGS. 1–5 illustrate the angioplasty catheter embodiment of the present invention, while FIG. 6 illustrates a second embodiment of a pressure differential sensor for diagnostic use (the therapeutic, dilation mechanism 18 is not present).

Figure 2A:
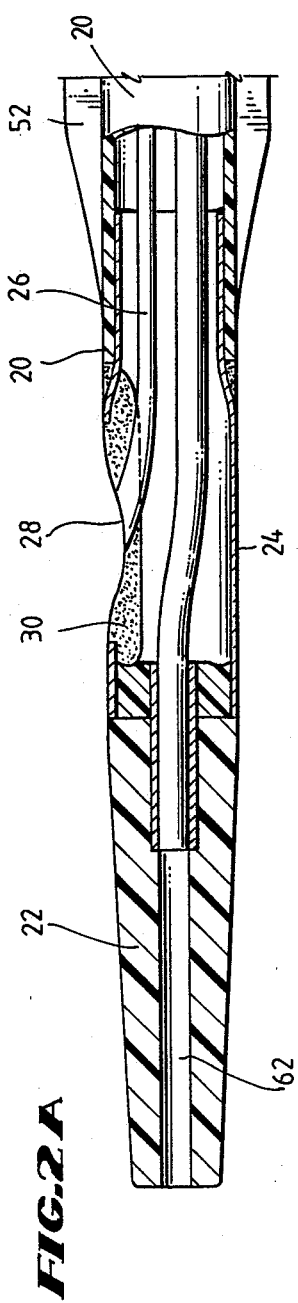
FIG. 2A is a fragmentary, enlarged, vertical sectional view of the distal end of the catheter of FIG. 1 taken along line 2A—2A of FIG. 1.

In more detail, the sensor mechanism 16 includes an elongated tubular housing 20 (FIG. 2A) which terminates in the low profile nose 22. A cylindrical support casing 24 (stainless steel) is spliced between the housing 20 and nose 22. An elongated tubular conduit 26 is received in the housing 20 and includes open end 28 positioned in a cutout portion of the casing 24 as shown in FIG. 2A. The end 28 of the conduit 26 is secured in this cutout portion by epoxy 30.

Figure 2B:
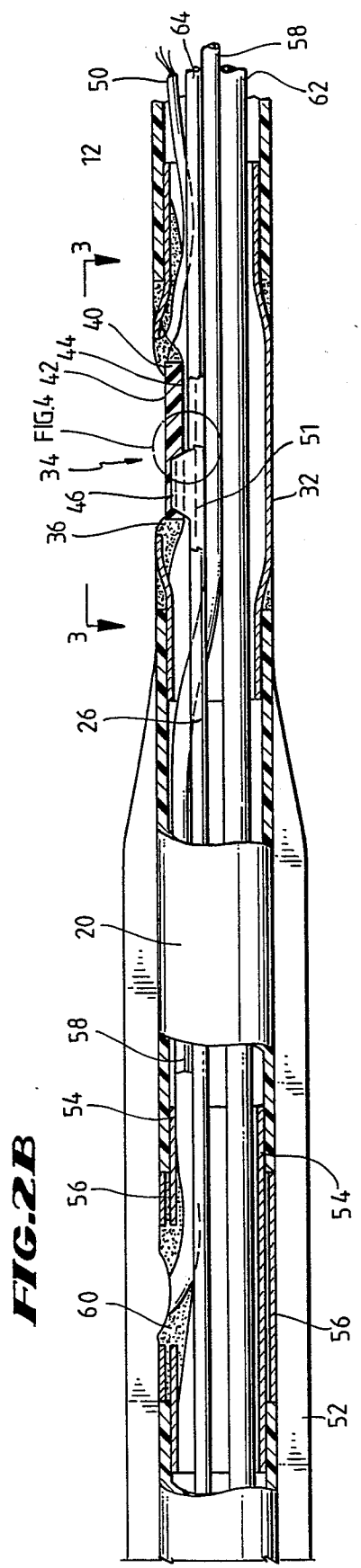
FIG. 2B is a fragmentary, enlarged, vertical sectional view of the proximal end of the catheter of FIG. 1 taken along line 2B—2B of FIG. 1.

Turning to FIG. 2B another stainless steel cylindrical casing 32 is joined to the housing 20 to provide a supporting structure. A transducer 34 is secured in a cutout portion of the casing 32 by the epoxy 36 as shown. Preferably, the transducer 34 is overlaid with a thin silicone rubber and epoxy mixture (not shown).

In more detail, the transducer 34 includes an elongated, plate-like semiconductor (e.g., silicon) member 40 having outer and inner surfaces 42, 44. That is, the outer surface 42 is oriented outwardly away from the casing 32, while the inner surface 44 is oriented into the interior of the casing 32. The semiconductor member 40 includes a weakened area which acts as a diaphragm 46. As shown in FIG. 3 strain gauges 48 are deposited on the member 40 (e.g., in a Wheatstone bridge arrangement) to respond to deformation of the diaphragm 46 to produce a signal indicative of that deformation. Electrical leads 50 connect to the strain gauges 48, and as shown in FIG. 2B are bundled in an insulator and received in the catheter body 12. Such semiconductor members 40 are commercially available, such as obtainable through Kulite, Inc. The transducer 34 is similar to those used in the MIKRO-TIP ® pressure transducer as sold by Millar Instruments of Houston, Texas (e.g., Model Nos. SPC-330,450). As can be seen from FIG. 2B, the conduit 26 terminates at end 51 adjoining the inner surface 44 of the member 40. In particular, end 51 is the enlarged region adjacent the diaphragm 46.

The dilation mechanism 18 includes an elongated (approximately 3 cm.) flexible, nonelastomeric, dilation balloon 52 which is expandable from an uninflated condition (not shown) to the inflated condition shown in FIG. 1 having a defined outer diameter (e.g. 3 mm). As can be appreciated from FIGS. 1 and 2B, an annular expansion region is defined between the housing 20 and dilation balloon 52. Stainless steel cylindrical casing 54 is spliced into the housing 20 as shown in FIG. 2B, and is enveloped by a radiopaque marker 56 positioned about midway within the balloon 52 (FIG. 1). The casing 54 and marker 56 are apertured to receive the open end of elongated cylindrical expansion lumen 58. As can be seen in FIG. 2B, the distal end of the expansion lumen 58 is secured in the aperture of the casing 54 and marker 56 by epoxy 60. The expansion lumen 58 extends from housing 20 and into the catheter body 12 leading to the interface section 14.

In the illustrated embodiment an elongated tubular structure defines passage 62 extending the length of the catheter of the apparatus 10 for shiftably receiving a steerable guidewire (not shown). As can be seen from FIG. 2A, the guidewire passage 62 extends from the nose 22 through the housing 20 and into the catheter body 12. It will be appreciated that other steering mechanisms can be incorporated into the present invention, such as the "Monorail" guidewire coupling system made by Schneider-Medintag of Zurich, Switzerland.

Turning to FIGS. 2B, 4, and 5, a structure defining an elongated filling lumen 64 is illustrated. As can be seen, the filling lumen 64 and end 51 of the conduit 26 are separated by a check valve structure 66. In the illustrated embodiment, the check valve structure 66 includes an upstanding stop 68 and a flexible flap 70 which can pivot away from the stop 68 in the direction of the conduit 26. The stop 68 prevents pivoting of the flap 70 in the direction of the filling lumen 64, preventing fluid flow in that direction.

As shown in FIG. 2B, the expansion lumen 58, guidewire passage 62, filling lumen 64, and electrical leads 50 are all received in the catheter body 12. The proximal end of the catheter body 12 leads to the interface section 12, terminating at Y-connector 72. The guidewire passage 62 extends through the Y-connector 72 to terminate at the Luer fitting 74, and is of course adapted for receiving a steerable wire guide. Similarly, the filling lumen 64 extends through the Y-connector 72 to terminate at the Luer fitting 76, while the expansion lumen 58 extends through the Y-connector 72 terminating at the Luer fitting 78. The electrical leads 50 extend beyond the Y-connector 72 to terminate at the adaptor/connector 80. The electrical leads 50 are connected through the adaptor/connector 80 through appropriate cables (not shown) to a strain gauge amplifier (not shown, such as commercially available from Hewlett-Packard or Spacelabs). In the illustrated embodiment, a transducer control unit, such as Model Nos. TC-510 or TCB 500 made by Millar Instruments of Houston, Texas would be interposed between the adaptor/connector 80 and the amplifier.

Turning to FIG. 6, an alternative embodiment is illustrated in which like numerals have been applied to features similar to the features of the embodiment of FIGS. 1-5. The embodiment of FIG. 6 is similar to the embodiment of FIGS. 1-5 except in two areas. First, the dilation mechanism 18 of FIGS. 1-5 is deleted. This illustrates that the sensing apparatus of the present invention is useful in a variety of applications other than being limited to angioplasty procedures. Second, the embodiment of FIG. 6 omits the filling lumen 64. That is, the conduit 26 extends from the end 28 at a distal location in the housing 20 and terminates at end 51 adjoining the inner surface 44 of the member 40.

In operation, the apparatus 10 illustrated in FIGS. 1-5 is introduced into the patient in a fashion similar to that used for conventional angioplasty catheters. That is, the apparatus 10 is introduced using the femoral or brachial approach through a guiding catheter which has its distal opening adjacent the ostium of the left or right coronary artery. A steerable guidewire (not shown) is threaded through the passage 62 and the apparatus 10 and guidewire progressively advanced through the guiding catheter. Appropriate flush and contrast injections are made for radiographic monitoring of the progression of the apparatus 10 in the coronary arterial tree.

Periodically contrast medium is introduced through the guidewire receiving passage 62 with or without removing the guidewire. The sensor mechanism 16 of the present invention allows the pressure differential between locations on each side of the dilation balloon 52 to be continuously monitored. That is, as soon as the apparatus 10 is introduced into the guiding catheter, a fluid is introduced through the Luer fitting 76 into the filling lumen 64 to purge the air and serve as a pressure transmission medium in the conduit. As illustrated in FIG. 5, the pressure of the fluid introduced into the filling lumen 64 biases the flap 70 allowing fluid to fill the conduit 26. With the conduit 26 filled with fluid, the pressure of the fluid in the conduit 26 is indicative of the fluid pressure at the end 28 of the conduit distal to the balloon 52. In addition, the conduit 26 may be used to inject medications or anticoagulants through the lumen 64 into the fluid vessel.

During insertion with the conduit 26 filled with fluid, a physician can continuously monitor pressure differential between the fluid (i.e., blood) adjacent end 28 and the fluid adjacent the transducer 34. That is, the diaphragm 46 deforms in response to differential fluid pressure adjoining the outer and inner surfaces 42, 44. The deformation of the diaphragm 46 generates a proportional signal in the strain gauges 48 which is connected to the amplifier external to the patient through the electrical leads 50.

The apparatus 10 of the present invention allows for continuous monitoring of pressure differential, helping safe cannulation of coronary arteries and prompt recognition of ischemia precipitated by the introduction of the contrast media or drugs, or inappropriate location of the nose 22. Preferably, a guidewire is steered subselectively past the ostium into the desired coronary artery into the region of stenosis and advanced across the lesion. The low profile nose 22 is then advanced along the guidewire and the position of the dilation balloon 52 monitored for placement adjacent the lesion. Advantageously, the pressure differential between locations on each side of the balloon 52 can be continuously monitored during this delicate advancement across the lesion. Transstenotic pressure gradient is, of course, a direct indication of the presence and degree of stenosis—the greater the pressure gradient, the more occluded the blood vessel.

With the dilation balloon 52 positioned adjacent a lesion diagnosed for angioplasty, the dilation mechanism 18 is operated to inflate the dilation balloon 52. A fluid under pressure, such as a mixture of contrast medium and saline solution, is introduced through Luer fitting 78 into the expansion lumen 58 to inflate the balloon 52. Progressive inflation of the balloon 52 hopefully distends the calcified sections of the lesion to at least partially alleviate the occlusion. Of course, transstenotic pressure gradient is continuously monitored during inflation to evaluate the efficacy of dilation.

The physician has many options using the apparatus 10 of FIGS. 1–5. For example, the physician may partially inflate the dilation balloon 52 to occlude the vessel to determine the extent of collaterization around the vessel. During such initial partial inflation, the pressure gradient between the end 28 and transducer 34 is useful for continuously monitoring the coronary wedge pressure and also useful in evaluating hyperemic response. Further, once the stenosis has been distended, the physician can determine the efficacy of treatment by monitoring the pressure gradient. If dilation has been satisfactory, the pressure gradient should be low (e.g., less than 15 mm Hg). However, if the pressure gradient remains high, additional inflations of the dilation balloon 52 are made, perhaps with incremental increases in pressure until the pressure gradient is satisfactorily low or cannot be improved with further inflations.

Operation of the embodiment of FIG. 6 is similar to the operation of the angioplasty catheter embodiment of FIGS. 1–5, but is useful in diverse applications. With the embodiment of FIG. 6, the physician will prefill the conduit 26 through open end 28 with fluid prior to inserting the apparatus 10 into the patient (e.g., through the guiding catheter). In the FIG. 6 embodiment, a guidewire (not shown) is similarly used for positioning the apparatus 10 in a desired region of interest. As the guidewire and apparatus 10 are advanced, the pressure differential between the end 28 and transducer 34 can be continuously monitored by the physician. For example, in a urological application the sensing mechanism 16 might be advanced into the urethra and a slow controlled withdrawal made to obtain an accurate urethral pressure gradient profile. The small size and low profile of the nose 22 allows easier introduction directly into the bladder.

Still further alternative embodiments of the present invention are possible without departing from the scope of the present invention. For example, the conduit 26 structure of FIG. 6 can be incorporated into the angioplasty catheter embodiment of FIGS. 1–5, eliminating the need for filling lumen 64. If the guidewire receiving passage 62 and filling lumen 64 are removed, the catheter body size and profile of nose 22 can be further reduced (e.g., on the order of 1 French).

As can be appreciated, the method and apparatus 10 in accordance with the present invention is extremely useful in sensing and monitoring the pressure differential in many medical applications. The apparatus 10 offers a small size and low profile for manipulation in very small openings or vessels. This pressure differential is obtained using a single transducer which provides not only high fidelity tracings, but also increases durability and reliability.

What is claimed is:

1. An apparatus for sensing the fluid pressure differential between two spaced apart locations in a fluid-filled biological vessel, comprising:
    an elongated housing;
    transducer means coupled to the ho using at a first location for sensing fluid pressure, and having a member which deforms in response to a fluid pressure differential thereacross and elongated leads operatively coupled to the member, the member presenting opposed outer and inner surfaces;
    an elongated catheter body coupled to the housing for receiving the leads; and
    structure defining a conduit coupled to the housing and having one end opening at a second location spaced from the first location and the other end adjoining the inner surface of the member,
    the housing being adapted for immersion in a fluid-filled biological vessel, with the housing immersed in the vessel, the second location being disposed within the biological vessel and the transducer means being operable for sensing the pressure differential between the fluid adjoining the outer surface of the transducer means and the fluid within the conduit adjoining the inner surface.

2. The apparatus according to claim 1, including structure defining a guidewire-receiving passage coupled to the housing.

3. The apparatus according to claim 2, the guidewise-receiving passage being disposed within the housing and catheter body.

4. The apparatus according to claim 1, including an expandable dilation balloon coupled to the housing and means for selectably expanding the balloon.

5. The apparatus according to claim 4, the first location being disposed proximal relative to the dilation balloon and the second location being disposed distal relative to the dilation balloon.

6. The apparatus according to claim 1, the first and second locations being longitudinally spaced along the housing at least 2 cm.

7. The apparatus according to claim 1, including structure defining a filling lumen running the length of the catheter body with an end in communication with the conduit, 8. The apparatus according to claim 7, including a check valve disposed between the filling lumen and conduit to permit fluid flow from the filling lumen into the conduit while preventing fluid flow from the conduit into the lumen.

9. The apparatus according to claim 1, the transducer means including one or more strain gauges mounted to the member and coupled to the leads.

10. The apparatus according to claim 9, the member having a diaphragm which deforms in response to a fluid pressure differential thereacross, the strain gauges being mounted to the member adjacent the diaphragm.

11. The apparatus according to claim 1, the conduit being disposed within the housing, the housing having a cutout portion at said second location for receiving said conduit at one end.

12. A method of sensing the pressure differential between two spaced-apart locations in a biological fluid-filled vessel comprising the steps of:
    providing a pressure sensor having a transducer, a catheter body coupled to the transducer, and an elongated conduit having one end adjoining the transducer and another end spaced from the transducer;
    inserting the sensor into the vessel with a portion of the catheter body extending externally from the vessel;
    manipulating the sensor to a region of interest in the vessel including the substeps of positioning the transducer at a first location in the vessel and positioning the conduit other end at a second location in the vessel spaced from the first location;

filling the conduit with fluid so that the fluid-filled conduit is indicative of the fluid pressure at the second location; and sensing, with the transducer positioned in the region of interest and the conduit filled with fluid, the pressure differential between the fluid adjoining one side of the transducer in the vessel at said first location and the fluid at said second location.

13. The method according to claim 12, said inserting step including the substeps of inserting a steerable guidewire having distal and proximal ends into the biological vessel, coupling the sensor to the guidewire, and advancing the sensor along the guidewire.

14. The method according to claim 13, including the steps of manipulating the guidewire into the coronary arterial tree with said distal end past a region of stenosis, and positioning the sensor with the conduit other end distal to the stenosis and the transducer proximal to the stenosis.

15. The method according to claim 14, including the step of dilating the stenosis, the sensing step occurring prior to, during, and after said dilating step.

16. The method according to claim 12, said filling step including the substep of injecting a fluid down a lumen in the catheter body, the lumen being in communication with the conduit.

17. The method according to claim 12, said filling step including the substep of drawing biological fluid through the conduit other end with the sensor inserted in the vessel.

18. The method according to claim 12, the sensing step including transmitting an electrical signal indicative of the pressure differential through electrical leads disposed within the catheter body and running external to the vessel.

19. An angioplasty catheter for sensing the blood pressure differential between spaced locations in a blood vessel, comprising:

an elongated catheter body;

a housing coupled to one end of the catheter body and adapted to be received in the blood vessel;

a guidewire-receiving passage coupled to the housing;

dilation means coupled to the housing and having a balloon selectably outwardly expandable from the housing; and means coupled to the housing for sensing the pressure differential between locations on each side of the balloon with the housing received in the blood vessel, including— a deformable member mounted to the housing proximal relative to the balloon and having an outer surface oriented outwardly away from the housing and an inner surface oriented inwardly into the housing, a conduit coupled to the housing having one end opening at a location distal relative to the balloon and another end adjoining the inner surface of the member, and means coupled to the member for indicating the deformation of the member in response to a blood pressure differential across the member, the indicating means including elongated electrical leads received in the catheter body.

20. The catheter according to claim 19, the guidewire-receiving passage being disposed within the housing and catheter body.

21. The catheter according to claim 19, including structure defining a filling lumen within the catheter body extending into the housing into communication with the conduit.

22. The catheter according to claim 21, including a check valve disposed between the lumen and conduit to permit fluid flow from the lumen into the conduit while preventing fluid flow from the conduit into the lumen.

23. The catheter according to claim 19, the deformable member including a diaphragm which deforms in response to a fluid pressure differential thereacross, the indicating means including one or more strain gauges mounted to the member adjacent to the diaphragm for indicating movement of the diaphragm.

24. The catheter according to claim 19, the dilation means including an expansion tube received within the catheter body and having one end opening into the balloon for selectably expanding the balloon.

25. In an elongated catheter having distal and proximal ends and a housing at the distal end adapted for insertion in a fluid-filled biological vessel, a pressure sensor wherein the improvement comprises:

a deformable member mounted to the housing at a first location and having outer and inner surfaces, an elongated conduit having one end opening at a second location spaced from the first location and another end adjoining said member inner surface, the member and conduit being cooperatively operable, when inserted in a fluid-filled vessel with the first and second locations disposed within the vessel, for the member to deform in response to a fluid pressure differential between the fluid proximate said first location and the fluid proximate said second location.

26. The improvement of claim 25, wherein said first location is proximal relative to said second location on the catheter.

27. THe improvement of claim 25, including an expandable dilation balloon coupled to the housing between said first and second locations.

28. The improvement of claim 25, including structure defining a guidewire-receiving passage coupled to the housing.

29. The improvement of claim 25, including structure defining a filling lumen running the length of the catheter with one end in communication with the conduit.

* * * * *